United States Patent [19]
Holsen

[11] Patent Number: 5,682,231
[45] Date of Patent: Oct. 28, 1997

[54] DEVICE AND METHOD FOR DETERMINING CONTAMINATION OF A LIGHT PERMEABLE MATERIAL UTILIZING THE VALUES OF DETECTED LIGHT BELOW THE SATURATION INTENSITY OF A SENSOR

[76] Inventor: John R. Holsen, 505 Christel Dr., Valders, Wis. 54245

[21] Appl. No.: 499,116

[22] Filed: Jul. 6, 1995

[51] Int. Cl.⁶ .......................... G01N 33/28; G01N 21/00; G01T 1/167
[52] U.S. Cl. .......................... 356/70; 356/364; 356/370; 356/442; 250/301
[58] Field of Search .................. 356/70, 73, 340, 356/341, 343, 439, 441, 442, 364, 370; 250/301

[56] References Cited

U.S. PATENT DOCUMENTS

| | | | |
|---|---|---|---|
| 3,510,666 | 5/1970 | Topol | 356/441 |
| 3,578,865 | 5/1971 | Traver | 356/70 |
| 3,892,485 | 7/1975 | Merritt et al. | 356/70 |
| 3,942,360 | 3/1976 | Wada | 73/61 R |
| 4,003,661 | 1/1977 | Yamano | 356/201 |
| 4,146,799 | 3/1979 | Pitt et al. | 356/70 |
| 4,201,471 | 5/1980 | Pitt et al. | 356/70 |
| 4,265,535 | 5/1981 | Pitt | 356/70 |
| 4,649,711 | 3/1987 | Sibley et al. | 62/129 |
| 4,699,509 | 10/1987 | Kamiya et al. | 356/70 |
| 4,957,363 | 9/1990 | Takeda et al. | 356/73 |
| 5,049,742 | 9/1991 | Hosonuma et al. | 250/301 |
| 5,266,800 | 11/1993 | Mullins | 356/70 |
| 5,309,213 | 5/1994 | Desjardins et al. | 356/70 |
| 5,506,679 | 4/1996 | Cooper et al. | 356/343 |

FOREIGN PATENT DOCUMENTS

| 2105028 | 3/1983 | United Kingdom | 356/70 |
|---|---|---|---|

*Primary Examiner*—David C. Nelms
*Assistant Examiner*—Jason D. Vierra Eisenberg
*Attorney, Agent, or Firm*—Andrus, Sceales, Starke & Sawall

[57] ABSTRACT

A device and method is provided for determining the degradation of oil after use of the same in an engine or the like. A test sample material is placed in a transparent container and various intensities of light are passed therethrough. A photovoltaic sensor senses the light polarized by the transparent container and the test sample and generates a first set of signals responsive thereto. The methodology is repeated with a sample of used automotive engine oil. The first and second set of signals are compared, and oil degradation is determined therefrom. Where the sensor detects and generates a signal only when the light intensity is equal to or less than the saturation intensity of the sensor, that is from the instant the light is first detected up until saturation of the sensor.

8 Claims, 1 Drawing Sheet

DEVICE AND METHOD FOR DETERMINING CONTAMINATION OF A LIGHT PERMEABLE MATERIAL UTILIZING THE VALUES OF DETECTED LIGHT BELOW THE SATURATION INTENSITY OF A SENSOR

BACKGROUND AND SUMMARY OF THE INVENTION

This invention relates to inspection of hydraulic and lubricating oil, and to quality control of many light transmitting substances, and, in particular, to a device and method for determining the degradation of oil after use of the same in an engine or the like.

The prior art includes two types of oil analyzers for the purpose of detection of contamination of the oil or impending chemical breakdown of the oil. These prior art devises are expensive and are limited to finding the value of a dielectric constant or some change in that constant in a single type of oil, i.e. hydraulic or lubricating. Consumers have little or no option except to submit samples to a party which specializes in analyzing oil, or change the oil at predetermined intervals to insure the quality of the oil.

Further, prior art oil analyzers partially destroy the oil sample and require high voltage to run the test. In addition, the high cost of prior art units increases the desire to create a portable unit. As such, an unresolved need exists for a method and an apparatus for determining the quality of a sample of light permeable material, such as oil, which is inexpensive and simple.

Therefore, it is a primary object and feature of the present invention to provide a simple, standard test for determining the quality of automotive engine oil.

It is a further object and feature of the present invention to provide a more robust and user friendly method and apparatus for testing the quality of oil which is able to interface with computers.

It is a still further object and feature of the present invention to provide a method and apparatus for testing the quality of oil which is simple and inexpensive to utilize.

Another object and feature of the present invention is to provide a method and apparatus for testing the quality of oil which is portable.

It is a still further object and feature of the present invention to provide a method and apparatus for testing the quality of oil which is nondestructive, and minimizes contact of the oil with the user.

It is a still further object and feature of the present invention to provide a method and apparatus for testing the quality of oil which does not require high voltage to perform the test.

In accordance with the present invention, a method and apparatus is provided for determining the degradation of a light permeable material after use of the same in an engine or the like. A first clean, unused sample of material and a second, used sample material to be tested are required. A light source generates light along the longitudinal axis. A transparent container is positioned along the longitudinal axis spaced from the light source for receiving each sample therein. A filter is positioned along longitudinal axis between the light source and the transparent container.

A photovoltaic sensor is positioned on an axis transverse to the longitudinal axis which extends through the transparent container. The sensor has a predetermined onset intensity corresponding to the minimum intensity light required for the sensor to generate a signal, and a predetermined saturation intensity wherein the signal generated by the sensor is constant.

Means are provided for varying the intensity of the light generated by the light source over a range of intensities having a lower limit corresponding to the onset intensity of the sensor and an upper limit corresponding to the saturation intensity of the sensor. Means are also provided for calculating the normal distribution of the signals generated by the sensor over the range of intensities of light generated by a light source, and for calculating the arithmatic mean of each normal distribution.

In operation, a first sample is placed in the transparent container. The light source generates a light which projects along the longitudinal axis. The intensity of the light is varied between the onset intensity of the photovoltaic sensor and the saturation intensity of the photovoltaic sensor. The light is attenuated with the filter and thereafter passes through the transparent container such that the attenuated light is polarized.

The photovoltaic sensor senses the polarized light over the range of intensities of light generated by the light source, and a first set of signals corresponding to the same is generated by the sensor. The normal distribution of the first set of signals generated by the sensor over the range of intensities is calculated and the arithmatic mean for the normal distribution is calculated thereafter.

The first, clean sample material is replaced in the transparent container with the second, used sample of material and the process is repeated such that the arithmatic mean of a second set of signals is calculated. Thereafter, the arithmatic mean of the first set of signals is subtracted from the arithmatic mean of the second set of signals, thereby providing the same as a contamination value. The contamination value is compared with a predetermined value such that if the contamination value is greater than the predetermined value, the second, used sample of material is deemed contaminated.

BRIEF DESCRIPTION OF THE PREFERRED EMBODIMENT

The drawing furnished herewith illustrates a preferred construction of the present invention in which the above advantages and features are clearly disclosed as well as others which will be readily understood from the following description of the illustrated embodiment.

FIG. 1 is a diagrammatic view of the apparatus of the present invention.

DETAILED DESCRIPTION OF THE PREFERRED EMBODIMENT

Figure 1:
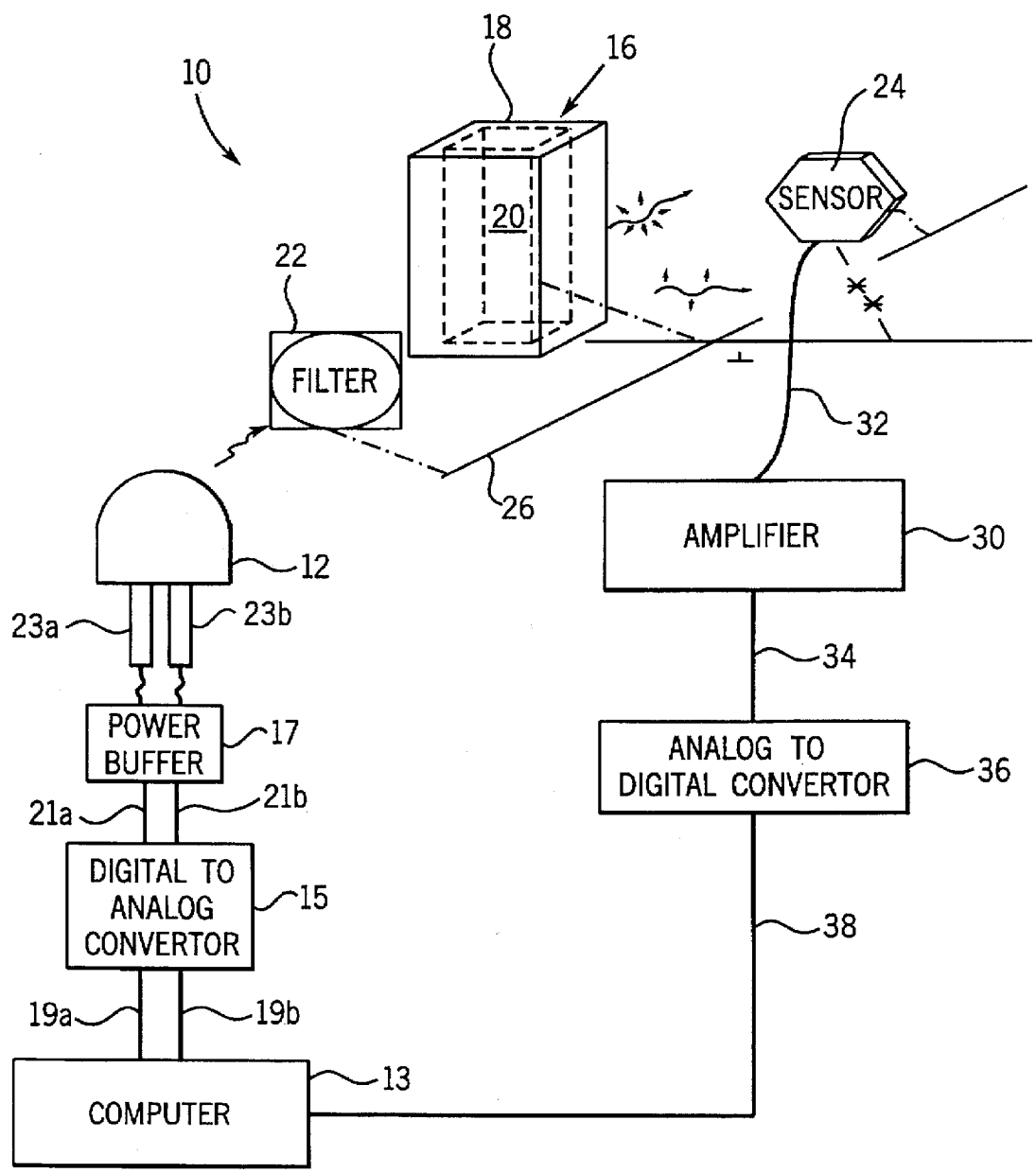

Referring to FIG. 1, the apparatus of the present invention is generally designated by the reference numeral 10. Apparatus 10 includes a light generating source 12 for generating light. In the preferred embodiment, light generating source 12 includes a red, light emitting diode.

Light emitting diode 12 is connected to a computer by a digital analog converter 15 and a power buffer 17. Computer 13 generates a signal along lines 19a and 19b to the digital analog converter 15. Digital analog converter 15 converts the digital signal along lines 19a and 19b to an analog signal on lines 21a and 21b which, in turn, passes through power buffer 17 and is interconnected to terminals 23a and 23b of emitting diode 12. In response to preprogrammed commands, the computer lights the light emitting diode 12 with varying intensities, for reasons hereinafter described.

A transparent container 16 is provided having a generally square cross-section. Container 16 includes an inner surface 18 which defines a cavity 20 within container 16. Cavity 20 also has a generally square cross-section, and is adapted for receiving an oil sample therein. In the preferred embodiment, container 16 is constructed from a transparent material such as glass or plastic.

A filter 22 is positioned between the light emitting diode 12 and container 16 so as to filter off high frequency oscillations generated by the light emitting diode 12 and to attenuate the same. For example, a 630 nanometer long pass red filter may be used. In a preferred embodiment, a sheet of red glass, 3 mm thick is used.

As best seen in FIG. 1, light emitting diode 12, filter 22, and container 16 lie along a single longitudinal axis 26 such that a light wave generated by light emitting diode 12 will pass through filter 22 and container 16.

A photovoltaic sensor 24 is placed at an angle of 90° to the light wave generated by the light emitting diode 12, and along an axis transverse to the longitudinal axis which extends through the transparent container 16. As is known, photovoltaic sensor 24 generates a voltage signal in response to light. Photovoltaic sensor 24 has a predetermined onset intensity which corresponds to the minimum intensity of light required to be sensed by photovoltaic sensor 24 to generate a voltage signal. In addition, photovoltaic sensor 24 has a saturation intensity corresponding to the intensity of light at which the photovoltaic sensor 24 begins to generate a constant voltage signal. At the saturation intensity of photovoltaic sensor 24, the sensor outputs approximately 2.3 volts. The 2.3 volts is a plateau, not a maximum sensor output.

In operation, a sample of a clean, unused light permeable material such as unused automotive engine oil is deposited within the cavity 20 of container 16. Computer 13 generates a signal along lines 9b to the digital analog converter 15. The digital analog converter 15 converts the digital signal along lines 9a and 9b to an analog signal on lines 21a and 21b which, in turn, passes from power buffer 17 to light emitting diode 12. In this manner, computer 13 lights light emitting diode 12 over a range of predetermined intensities. These intensities lie between the onset intensity and the saturation intensity of the photovoltaic sensor 24.

As the light travels along the longitudinal axis, it passes through filter 22. Filter 22 filters out high frequency oscillations generated by the light emitting diode 12 and attenuates the light. The attenuated light passes through the transparent container 16 such that the attenuated light is polarized by the container 13 and the sample therein.

Photovoltaic sensor 24, placed on an axis transverse to the longitudinal axis and passing through container 16, receives the polarized light and generates a voltage signal responsive to the intensity of the light received by the photovoltaic sensor 24. Since computer 13 varies the intensity of the light generated by the light emitting diode 12, a first set of signals is correspondingly generated by photovoltaic sensor 24 responsive to each intensity of light produced by light emitting diode 12 and generated by computer 13.

Photovoltaic sensor 24 is connected to an amplifier 30 by line 32 such that each signal generated by sensor 24 is amplified by amplifier 30. The amplified signal passes along line 34 to an analog to digital converter 36 which converts the amplified analog voltage signal to a digital signal. The digital signal is transmitted along line 38 to computer 13 wherein the computer calculates the normal distribution of the first set of signals generated by the photovoltaic sensor 24 over the range of intensities produced by light emitting diode 12.

After computer 13 calculates the normal distribution of the first set of signals generated by the photovoltaic sensor 24, the range defined between the onset intensity of photovoltaic sensor 24 and the saturation intensity of photovoltaic sensor 24 is modified to insure consistent results and eliminate errors associated with the onset and the saturation of photovoltaic sensor 24. In the preferred embodiment, computer 13 calculates the arithmatic mean of the first set of signals corresponding to the central one third portion of the range of intensities.

The initial clean, unused sample of light permeable material is replaced with a sample of used, light permeable material such as used automotive engine oil, and the process described above is repeated such that a second set of signals is generated by the photovoltaic sensor 24 and a arithmatic mean, corresponding to this second set of signals over the central one-third portion of the range of intensities, is calculated by computer 13.

The arithmatic mean corresponding to the first set of signals is subtracted by the arithmatic mean corresponding to the second set of signals resulting in a contamination value. This contamination value is compared to a predetermined replacement value such that if the contamination value exceeds the replacement value, the used automotive engine oil is replaced. On the other hand, if the contamination value is less than the predetermined replacement value, use of the used automotive engine oil is continued in the automotive engine.

Various modes of carrying out the invention are contemplated as being in the scope of the following claims, particularly pointing out and distinctly claiming the subject matter regarded as the invention.

I claim:

1. A method for determining the difference in contamination between a reference sample and a test sample of an oil material, comprising the steps of:

placing the reference sample in a transparent container;

generating light along a longitudinal axis;

providing a photovoltaic sensor, the sensor generating a constant signal in response to an intensity of light equal to or greater than the saturation intensity;

varying the intensity of the light over a detection range of intensities less than the saturation intensity of the photovoltaic sensor;

attenuating the light with a filter;

passing the attenuated light through the transparent container to cause polarization of the attenuated light;

sensing the polarized light with the photovoltaic sensor, the sensor generating a first set of signals corresponding to the range of intensities of light generated by the light source;

calculating a normal distribution of the first set of signals generated by the sensor;

calculating an arithmetic mean of the normal distribution of the first set of signals;

replacing the reference sample of the oil material in the transparent container with the test sample of oil material;

varying the intensity of the light once again over the detection range of intensities;

attenuating the light with the filter;

passing the attenuated light through the transparent container to cause polarization of the attenuated light;

sensing the polarized light with the photovoltaic sensor, the sensor generating a second set of signals corresponding to the intensity of light generated by the light source;

calculating a second normal distribution of the second set of signals generated by the sensor;

calculating a second arithmetic mean of the second normal distribution of the second set of signals; determining a contamination value by subtracting the arithmetic mean of the normal distribution of the first set of signals from the second arithmetic means of the second set of signals; and comparing the contamination value with a predetermined value such that if the contamination value is greater than the predetermined value, the test sample of oil material is deemed contaminated.

2. The method of claim 1 wherein each step of attenuating the light filter includes the step of filtering out high frequency oscillation generated by the light source.

3. A method for determining the difference in contamination between a first sample and a second reference sample of oil material, comprising the steps of:

providing a photovoltaic sensor, the sensor generating a constant signal in response to an intensity of light equal to or greater than the saturation intensity;

passing light through the first sample so as to cause polarization of the light;

sensing the polarized light with a photovoltaic sensor;

varying the intensity of the light over a range of intensities less than the saturation intensity of the photovoltaic sensor;

generating with the sensor a first set of signals corresponding to the range of intensities;

passing light through the second sample so as to cause polarization of the light;

sensing the light polarized by the second reference sample with the photovoltaic sensor;

varying the intensity of the light over the range of intensities;

generating with the sensor a second set of signals corresponding to the range of intensities generated by the light source; and comparing the first set of signals to the second set of signals to determine contamination.

4. The method of claim 3 comprising the further step of placing the first sample in a transparent container before passing light through the first sample.

5. The method of claim 3 comprising the further step of placing the second sample in a transparent container prior to passing light through the second sample.

6. The method of claim 3 comprising the additional step of attenuating the light with a filter prior to passing the light through the first sample.

7. The method of claim 3 comprising the further step of attenuating the light with a filter prior to passing the light through the second sample.

8. The method of claim 3 wherein the step of comparing the first set of signals to the second set of signals includes the additional steps of:

calculating the normal distribution of the first set of signals over the range of intensities;

calculating the arithmatic mean of the normal distribution of the first set of signals;

calculating the normal distribution of the second set of signals over the range of intensities;

calculating the arithmatic mean of the normal distribution of the second set of signals; and comparing the difference between the arithmatic mean of the first set of signals and the arithmatic mean of the second set of signals.

* * * * *